United States Patent [19]

Slomski

[11] 3,972,132
[45] Aug. 3, 1976

[54] DEVICE TO DETECT HAND TREMORS OF VARIOUS CAUSES

[76] Inventor: Waclaw Kazimierz Slomski, 426 Wilkinson St., Syracuse, N.Y. 13204

[22] Filed: Jan. 28, 1975

[21] Appl. No.: 544,205

[52] U.S. Cl. ............................................. 35/22 R
[51] Int. Cl.² .......................................... G09B 19/00
[58] Field of Search ............... 35/22 R, 11; 273/1 E; 128/1 C, 25 A

[56] References Cited
UNITED STATES PATENTS

| | | | |
|---|---|---|---|
| 3,029,526 | 4/1962 | Olalainty | 35/22 R |
| 3,030,944 | 4/1962 | Blau et al. | 35/22 R X |
| 3,641,686 | 2/1972 | Krass | 35/22 R |

OTHER PUBLICATIONS

C. H. Stoelting Co. Catalog, Jan. Title Index page, pp. 59 and 60, available in G.A.U. 334.
C. H. Stoelting Co. Catalog; January, 1974. Indexpage, p. 7, available in G.A.U. 334.

*Primary Examiner*—William H. Grieb
*Attorney, Agent, or Firm*—Mason, Mason & Albright

[57] ABSTRACT

This device tests drivers of all kinds of motor vehicles psychologically, and can be also used in a variety of different situations. It includes the following main components:

a. Arrangement of two measuring levers at a certain angle to each other; the inner rims of the levers form a measuring scale, which is connected by wires to a recording device.

b. Optical interference device in the form of a rotating disc on which certain lines are painted.

c. Probe.

d. Recording Scale.

The tested subject holds the probe in his hand and leads it between the two measuring levers, starting from the wider end towards the narrow end. Behind the measuring levers is a rotating disc which serves as an optical interference device. Each contact of the probe with the measuring levers is recorded electrically on the recording scale.

10 Claims, 6 Drawing Figures

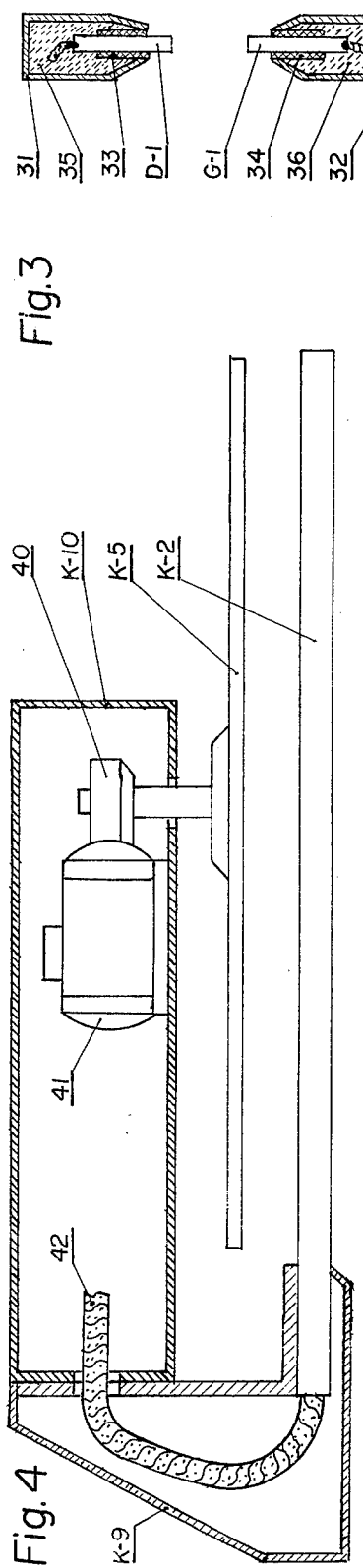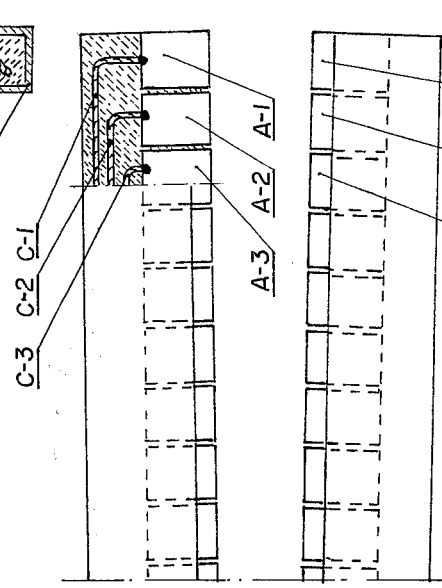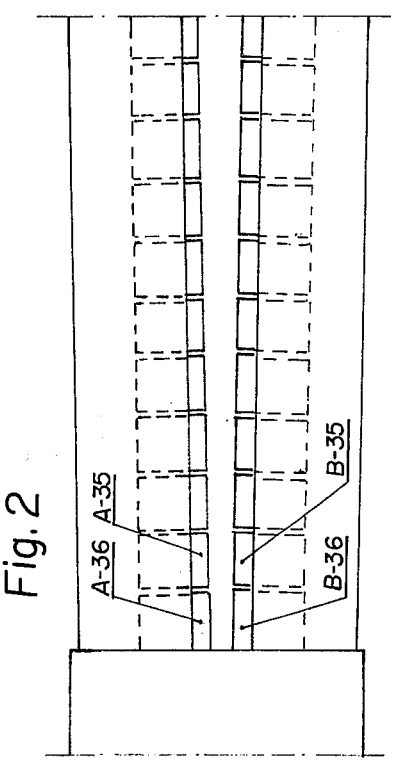

DEVICE TO DETECT HAND TREMORS OF VARIOUS CAUSES

BACKGROUND OF THE INVENTION

The enormous development of street and highway traffic results in a steadily growing number of traffic accidents. These accidents bring about great material losses and, first of all, are incommensurable in relation to human losses; loss of life, or permanent invalidism. The safety of traffic on the highways and streets depends to a considerable degree on the fact that a driver will succeed in a definite traffic situation to react in a proper way, and sufficiently fast. The psychology of street and highway traffic attempts to explain these problems. The subject of its investigation is a detailed analysis of the driver's work, to establish psycho-physiological functions indispensable for its safe execution. The driver's work has a specific character. In addition to some acquired information, training and possession of driving competence, the driver is also required to possess a particular psycho-physiological competence, considering the dynamics of the driven vehicle, and the human life and health hazards connected with it.

Among the great number of drivers traveling on the streets and highways there are some, who often do not realize that they have certain psycho-physiological deficiencies. This is why a necessity arises for controlling psycho-physiological characteristics of drivers before their licensing and during their execution of work as concerns changes or disappearance of psycho-physiological competence.

The proper evaluation of psycho-physiological characteristics of a driver can be made only by using certain types of testing apparatus, specialized and adapted for this aim. One such apparatus to serve such aims is my present invention. It can be used for studying the precision of motions connected with the tremor of hands which appears with illnesses of the nervous system, alcoholism, and old age. This device has been already successfully tested in several cases for determining the presence and degree of such afflictions.

DETAILED DESCRIPTION

The invention comprises the feature of construction, combination of elements, and arrangements of parts, which will be exemplified in the construction hereinafter set forth, and the scope of the invention will be indicated in the claims.

The invention has a wide application for testing people; it permits studying the precision of hand and arm motion and of the related tremors of the hands, which appear in afflictions of the nervous system, in alcoholism, neurosis, and also in old age. This device is intended primarily for psychological testing of drivers of all types of motor vehicles, as well as of other people, either in qualifying tests for candidates in various professions, or for controlling tests for people already employed (industrial tests).

The equipment forms a part of a group of other testing instruments which together form a set of equipments for a method of psychological tests for drivers. These tests are aimed at reducing the number of traffic accidents and thus increasing the safety on the streets and highways.

Figure 1:
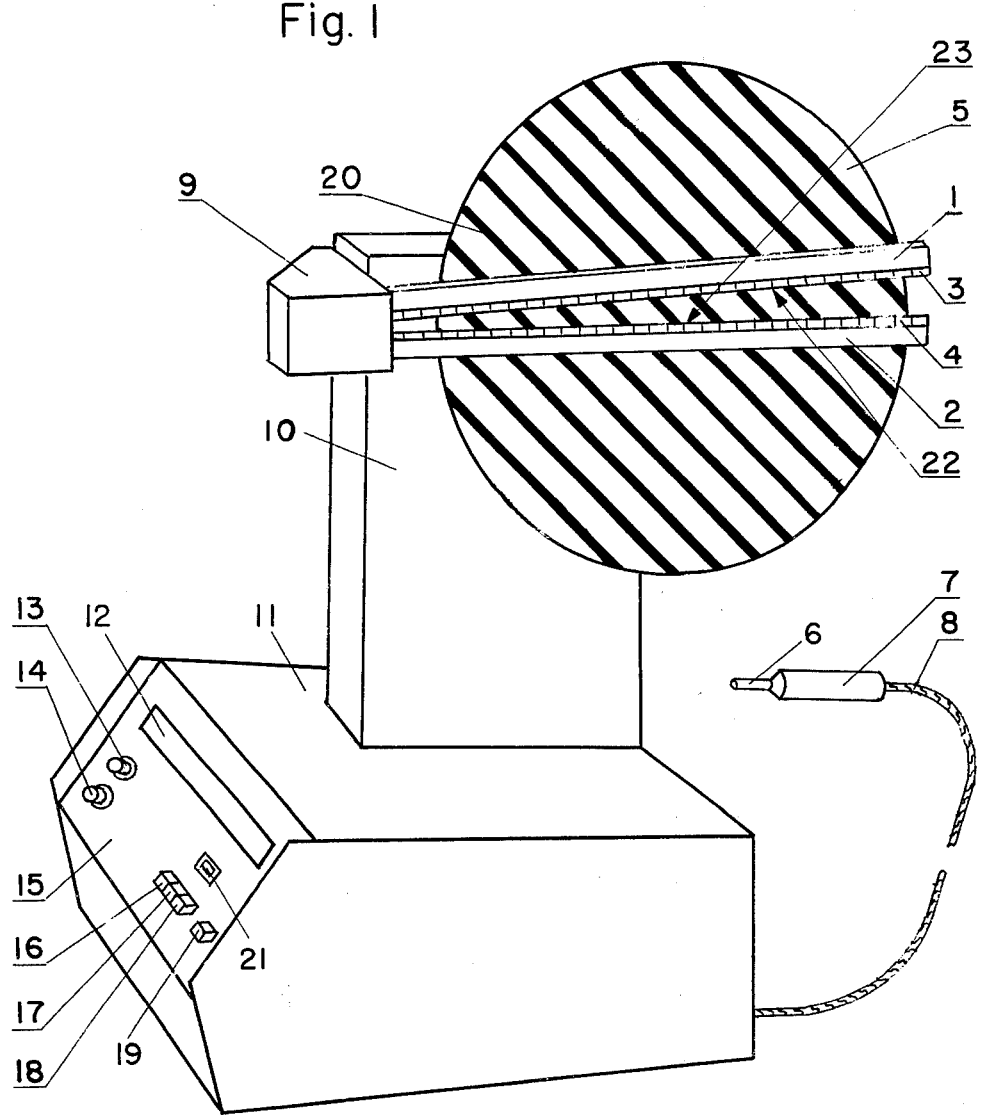

For a fuller understanding of the nature and objects of the invention, reference should be had to the following detailed description, taken in connection with the accompaying drawings, in which:

FIG. 1 — Perspective view of the apparatus of the invention, shown from the side of the tested person.

FIG. 2 — System of measuring levers.

FIG. 3 — Section of measuring elements of the lever: the contact plates.

FIG. 4 — Cross-section of the driving mechanism of the disturbing stimulus of the measuring levers, and of the disc of the disturbing stimulus.

FIG. 5 — View of the recording scale.

Figure 6:
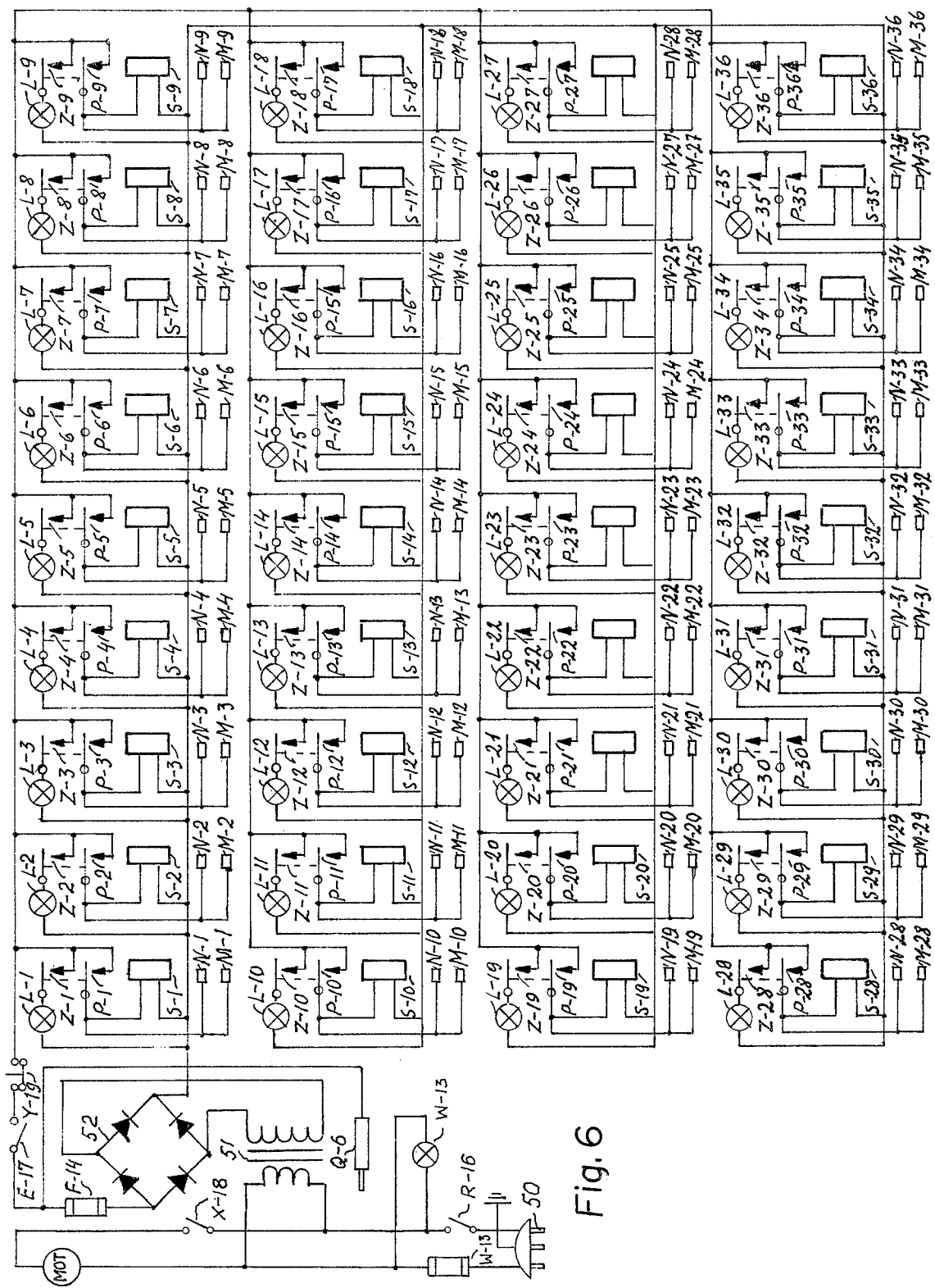

FIG. 6 — Wiring diagram of the electric system of the equipment.

FIG. 1 presents in perspective a general view of the equipment with all its elements: controlling, measuring and driving. All the electrical elements are placed in the equipment casing 11. They serve for driving and controlling the operation of the equipment. The front plate 15 is located on the casing 11, and on this plate are fixed the following elements: the recording scale 12, which registers the results of the tests; the four-position push-button switch, where the switch 16 serves for starting the system; a signal lamp 21, signaling that the system is in operation; switch 17 for switching on the supply of current; switch 18, for starting the disc 5 of the disturbing interference; switch 19 for cancelling the results of the test from the recording scale 12; the fuse socket 13 of the network and the fuse socket 14 of the electric feeding system of the equipment.

From the back of the equipment casing 11 extends a conductor 8, at the end of which an electric probe 6 is placed in a protective insulated shield 7.

On the upper wall of the casing 11 a metal column 10 is fixed, in the upper part of which the following elements are located: a system of two measuring levers in the form of a double-arm lever: the upper lever 1, and the lower lever 2, and their thirty six upper and thirty six lower contact plates, where one plate of the upper lever is marked as 3, and one plate of the lower lever is marked as 4. A shield 9 covers the fastening of the measuring lever; the disc of the interference stimulus 5, on which as an example, black stripes 20 on a white background are shown; this disc is exchangeable, one can utilize different discs with a variety of designs, such as a black spiral on white background, etc.

The measuring levers 1 and 2 are placed at an angle between themselves, forming a certain acute angle. The entrance leading between the levers 1 and 2 is somewhat wider than the space further along between such levers. The ends of the measuring levers thus approach closer together, so that the last contact plates of the double-arm lever, A36 and B36 near the edge of the cover 9, are separated at a distance almost equal to the diameter of the probe 6 (the clearance between the last contact plates and the probe 6 - the play - is circa 0.5 mm). TESTING METHOD. The tested person holds the probe 6 by its casing 7. The tested person has to guide the probe along the slot between the two arms 1 and 2 of the levers starting from the wider opening between them and proceeding towards the point where the arms join.

The probe has to be guided in such a way as not to touch any one of the contact plates of the levers 1 or 2. Every touching of the probe 6 with any one of the contact plates is electrically registered on the recording scale 12, where a signal lamp L1, L2, . . . . L35, L36, is switched on by the corresponding relay S1, S2 . . S3 . . . S35, S36, see FIG. 6. The lamps illuminate a corresponding number on the recording scale 12, which fact is considered as an error for the tested person. The farther the numbers are from the wider opening of the double-arm measuring lever, the smaller is the error, considering that at the end of the angle near the column 10, the distance between the last upper and lower contact plates is almost exactly equal to the diameter of the probe 6. Also it is to be noted that, the recording scale shows not only the distance of the contact plate from the beginning of the test range, but also registers the quantity of plates touched. The probe 6 has to be held in such a way that the forearm of the tested person will not rest either on a support or on any part of the tested person's body. During the test, the disc 5 rotates at various speeds, thus creating a disturbing interference.

FIG. 2 represents a view of the measuring levers 1 and 2. Their electric contact plates, the upper A1, A2, A3 . . . A36, and the lower B1, B2, B3, . . . B36, constitute the basic elements of the double-arm lever 1 and 2. These contacts are made from plates of metal with good electric conductance. They are electrically isolated from each other; their length along the run of the levers is approximately 10 mm each. The separate borders of the contact plates of each lever are located on one level, and form a straight line on all its measuring length, which is marked 22 for the upper lever, and 23 for the lower one.

Every contact plate of the upper and the lower levers is connected with an electric cconductor. As an example, a cut has been made in the right-hand cover of the upper lever, exposing three contact plates: A1, A2, and A3, and also three conductors: C1, C2, C3, which are soldered to the tops of the contact plates. The conductors of the contact plates of the lower lever are connected in the same way as of the upper one. All the contact plates, together with their conductors, are enclosed in casings. The upper lever's casing is marked 31, the lower's as 32, see FIG. 3. All contact plates together with their conductors are sealed in epoxy resin.

All conductors outgoing from the separate contact plates of the upper lever, and the corresponding conductors outgoing from the corresponding plates of the lower lever, are joined in pairs. Thus every contact plate of the upper level is connected electrically with every corresponding contact plate of the lower lever. For example, the contact plate A1 of the upper lever is connected by an electric conductor with the contact plate B1 the lower lever; similarly, the plate A2 is connected with the plate B2, A3 with B3, etc.

FIG. 3 represents a cross-section of both levers, made between two contact plates of the levers: D1 and G1 are the contact plates; 31 and 32 are the metal covers of the upper and the lower levers; 33 and 34 are the insulation layer, which separates the contact plates in the same lever from each other; 35 and 36 are the epoxy resin, in which the contact plates of the levers are sealed together with their electric conductors.

FIG. 4 represents a plane section made across the rotation axis of the disturbing interference disc. There, we see the electric drive 41 of the interference disc, the transmission gear 40 of the drive 41, the column K10, the interference disc K5, the lower measuring lever K2, and a multicore cable 42, which consists of the separate conductors, and leads to the relays, see FIG. 6.

FIG. 5 represents the recording scale 12, see FIG. 1, which registers results of the tests. The scale is made of plexiglass. Its reverse side is painted in black, and numbers from 1 to 36 are engraved on it. The number 1 on the scale corresponds to the two first contact plates A1 and B1 of the upper and the lower levers 1 and 2 of the double-arm lever, see FIG. 2. Every following number on the indicating scale corresponds to the following corresponding pair of contact plates of the double-arm lever 1 and 2.

FIG. 6 represents the electric connections diagram of the equipment which is supplied from the 115-V, 60 Hz network. Fast-operating electric relays S1, S2, S3, . . . S36, constitute the 36 basic electric elements of the equipment. All relays have identical electric parameters, and the same number of contacts each, i.e., two pairs of break contacts per relay. One pair of contacts serves for maintaining the switching of the given relay, while the second pair serves for switching on the indicating lamp on the indicating scale 12, see FIG. 5, which corresponds to the contacted plates of the measuring levers 1 and 2. The contact plates of the upper lever N1, and of the lower lever M1, which corresponds on FIG. 2 to contact plates A1 and B1, have their separate relay S1. Thus, each relay serves two contact plates of the measuring levers 1 and 2. For example, the first contact plate of the upper lever N1 is connected by the electric conductor C1 of FIG. 2 with the contact plate M1 of the lower lever; the contact plate N2 is connected with the contact plate M2 etc, and finally, the contact plate N36 is connected electrically with the contact plate M36. The touching of the N2 or M2 contact plates by the probe Q6 causes the operation of the corresponding relay S2.

After plugging the equipment into the 115-V/60-Hz network 50, and switching on the switch R16, the transformer 51, and the diode converter system 52 become connected with each other. This operation is signaled by the control lamp H21. After the connecting of the switch E17, all the testing system is under a 24-V d-c current. The switch X18 serves for switching the drive of the disk of the disturbing stimulus. The W13 fuse serves for protecting the 115-V network, and the fuse F14 serves for protecting the 24-V d-c network. Every pair of contact plates N1, and M1, N2 and M2, etc., . . . N36 and M36, are controlled by one separate relay, S1, S2, etc., . . . S36. Every individual relay has two pairs of break contacts, P1 and Z1, P2 and Z2, etc., . . . P36 and Z36. Contacts P1, P2, P3, etc., up to P36, serve for maintaining the switching in of the given relay. Contacts Z1, Z2, Z3, . . . Z36, serve for switching on the indicating lamps L1, L2, etc., up to L36, on the recording scale 12, see FIG. 5.

The tested person holds the probe Q6, and leads it between the contact plates N1 and M1, N2 and M2, N3 and M3, etc., . . . up to N36 and M36, at the end of the double-arm measuring lever 1 and 2. If the tested person will touch during the test any contact plate with the probe Q6, for example N23, then the relay S23 will be switched on, and will connect the contacts P23, which maintain the switching in of the S23 relay, and the Z23 contacts will switch on the indicating lamp L23 on the recording scale, and the FIG. 23 on the scale will be lighted from below the scale, see FIG. 5, indicating that the touching occurred at a distance of the 23rd centimeter from the beginning of the measuring lever. The same will occur with any further upper or lower contact plate, giving at the end of the test not only the number of contact plates touched by the probe Q6, but also their distances from the beginning of the measuring lever.

After having recorded the results of the test from the recording scale 12, see FIG. 1, these results have to be cancelled from the scale by pressing the trip button Y19, which breaks the current supply to the relays; then the relays are de-energized and the contacts maintaining the relays at this time, as well as the contacts switching on the indicating lamps of the recording scale 12, become disconnected. In this way, the first cycle of the test comes to an end and the equipment is prepared for another measuring cycle.

By analyzing the results obtained during the tests, one can evaluate the given person as to the possession of the necessary characteristics of the given psycho-physiological function, and thus one will have evidence to anticipate good or bad results by this person for the task he has applied.

The above described equipment has been built in a model. All its electric and mechaical systems operate accurately, and perfectly meet the requirements. The equipment can unreservedly be used for psychological tests.

Having described my invention what I claim as new and desire to secure by Letters Patent is:

1. In psychological testing apparatus, a device comprising a pair of measuring levers which are spaced apart to define a longitudinal slot opening between them, each said lever including electrical conductive means extending along said opening, each said conductive means including location discrimination means, electrically conductive probe means adapted to be received in said opening whereby it need not touch either said measuring lever, an electrical circuit means interconnecting said discrimination means with said probe means, an indicator means connected in said circuit means so that it automatically registers the distance along said opening where said probe touches at least one of said discrimination means, and handle means connected to said probe means whereby it is manually movable within said opening.

2. A device in accordance with claim 1 wherein said opening has an entrance at one end and diverges towards the other end.

3. A device in accordance with claim 1 wherein said discrimination means comprises a series of segments, each said segment having a separate electrical connection to said circuit means.

4. A device in accordance with claim 1 wherein an optical interference device is associated with the apparatus.

5. A device in accordance with claim 4 wherein said interference device comprises a rotating disc with a design for creating an optical interference thereon.

6. A device in accordance with claim 5 wherein said rotating disc is removable and exchangeable with a further disc with different designs applied thereon.

7. A device in accordance with claim 5 wherein said rotating disc is interconnected to a transmission gear adapted to control the rotating speed of said disc.

8. A device in accordance with claim 5 wherein said rotating disc is placed behind said measuring levers in such a way that testing is conducted with said rotating disc in the background.

9. A device in accordance with claim 1 wherein said discrimination means in each said lever comprises a row of contact plates, said plates on each lever forming a straight line defining said opening and being coplanar.

10. A device in accordance with claim 9 wherein each said plate is electrically insulated from each other said plate in each lever and forms a separate electrical contact in each said lever.

* * * * *